US009084873B2

(12) United States Patent
Lampropoulos et al.

(10) Patent No.: US 9,084,873 B2
(45) Date of Patent: Jul. 21, 2015

(54) INFLATION DEVICES AND METHODS OF USE THEREOF

(71) Applicant: Merit Medical Systems, Inc., South Jordan, UT (US)

(72) Inventors: Fred Lampropoulos, Salt Lake City, UT (US); Jim Mottola, Salt Lake City, UT (US); Brian Stevens, Pleasant Grove, UT (US); Steven Weir, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 14/031,746

(22) Filed: Sep. 19, 2013

(65) Prior Publication Data
US 2014/0088499 A1  Mar. 27, 2014

Related U.S. Application Data

(60) Provisional application No. 61/704,342, filed on Sep. 21, 2012.

(51) Int. Cl.
*A61M 25/10* (2013.01)
(52) U.S. Cl.
CPC ..... *A61M 25/10182* (2013.11); *A61M 25/1018* (2013.01); *A61M 25/10181* (2013.11); *A61M 25/10184* (2013.11); *A61M 25/10187* (2013.11); *A61M 25/10188* (2013.11); *Y10T 29/49815* (2015.01)
(58) Field of Classification Search
CPC ................... A61M 25/10182; A61M 25/1018; A61M 25/10181; A61M 25/10184; A61M 25/10187; A61M 25/10188

USPC ........ 604/97.01, 97.02, 97.03, 99.01, 100.01, 604/100.03, 218, 220, 223, 224
See application file for complete search history.

(56) References Cited

U.S. PATENT DOCUMENTS

| 3,606,094 | A | * | 9/1971 | Mills et al. ................. 222/145.6 |
| 4,476,866 | A | | 10/1984 | Chin |
| 4,758,223 | A | | 7/1988 | Rydell |
| 4,929,238 | A | | 5/1990 | Baum |
| 5,209,732 | A | | 5/1993 | Lampropoulos et al. |
| 5,306,248 | A | * | 4/1994 | Barrington ................. 604/97.02 |
| 5,752,935 | A | | 5/1998 | Robinson et al. |
| 6,793,660 | B2 | | 9/2004 | Kerr et al. |
| 7,717,880 | B2 | | 5/2010 | Denolly |
| 2010/0185156 | A1 | | 7/2010 | Kanner et al. |

FOREIGN PATENT DOCUMENTS

| WO | WO00/78386 | 12/2000 |
| WO | WO2012/094403 | 7/2012 |

OTHER PUBLICATIONS

International Search Report and Written Opinion dated Dec. 18, 2013 for PCT/US2013/060641.
International Search Report and Written Opinion dated Dec. 18, 2013 for PCT/US2013/060062.
International Preliminary Report dated Apr. 2, 2015 for PCT/US2013/060062.
International Preliminary Report dated Apr. 2, 2015 for PCT/US2013/060641.

* cited by examiner

*Primary Examiner* — Manuel Mendez
(74) *Attorney, Agent, or Firm* — Stoel Rives LLP

(57) ABSTRACT

Inflation devices and methods to inflate medical devices are disclosed. Certain embodiments enable the selective coupling of a plunger to a syringe body through manipulation of a handle. Other embodiments facilitate the generation of relatively high fluid pressures through inflation device designs that incorporate multiple plungers.

22 Claims, 8 Drawing Sheets

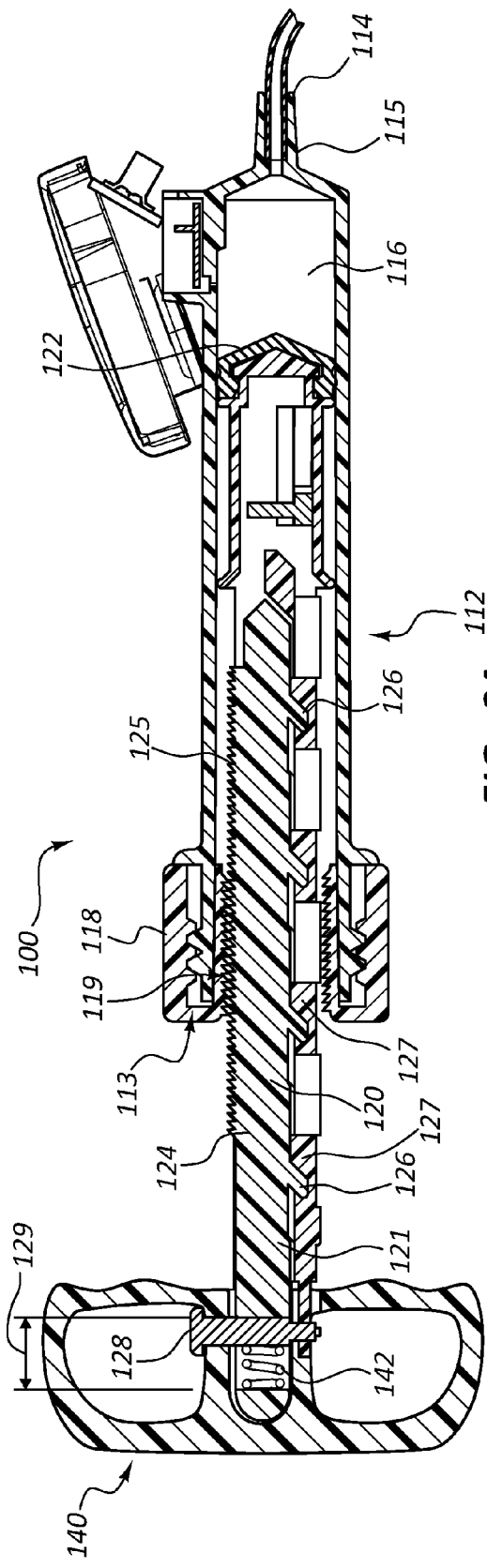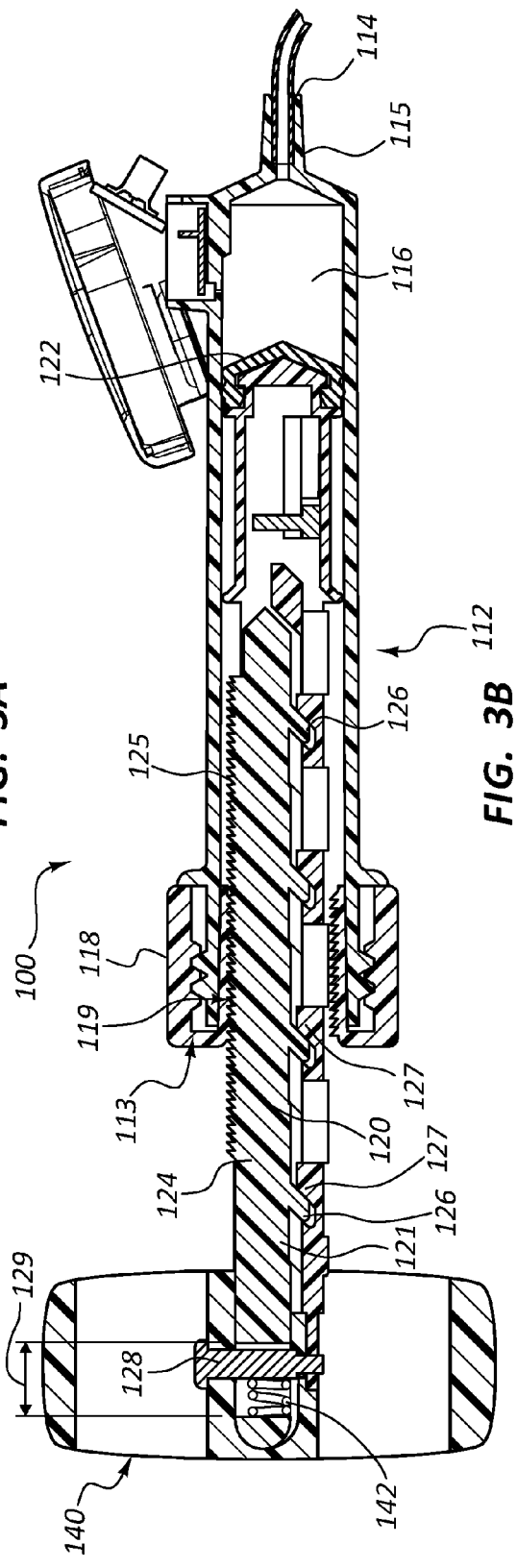
FIG. 3A
FIG. 3B

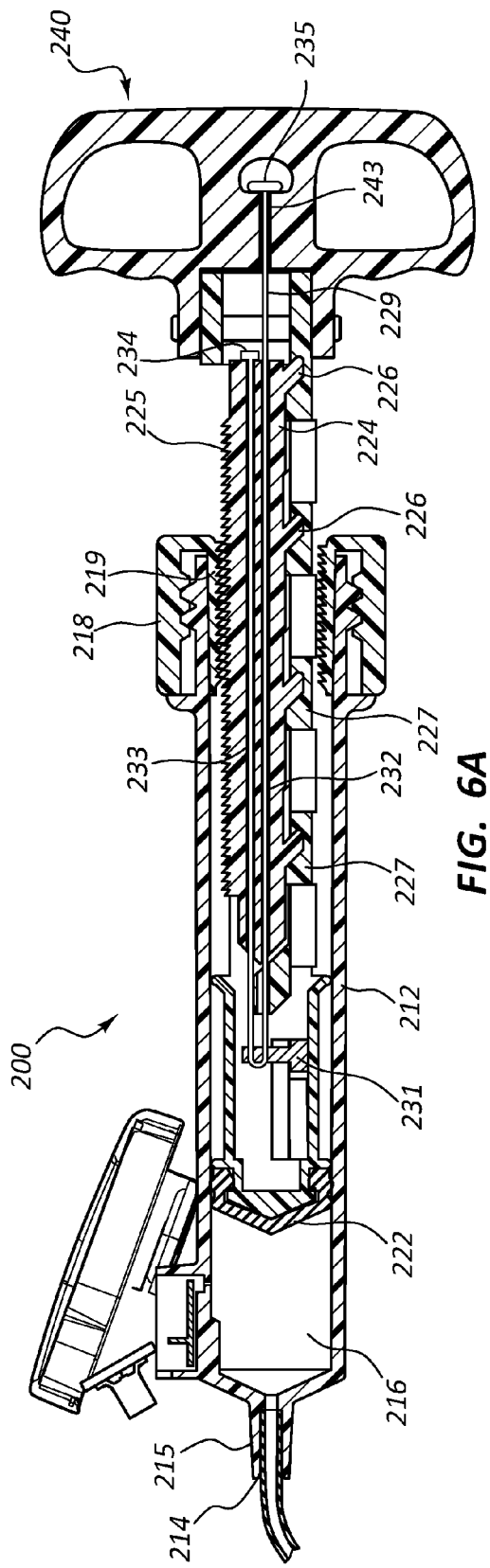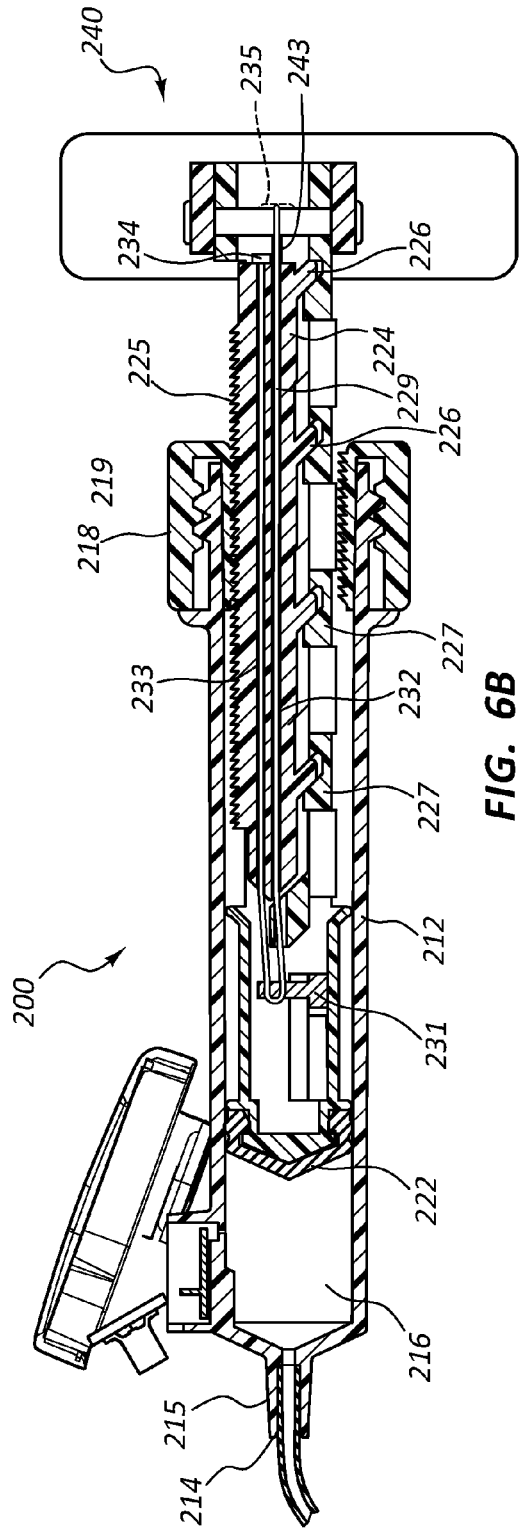

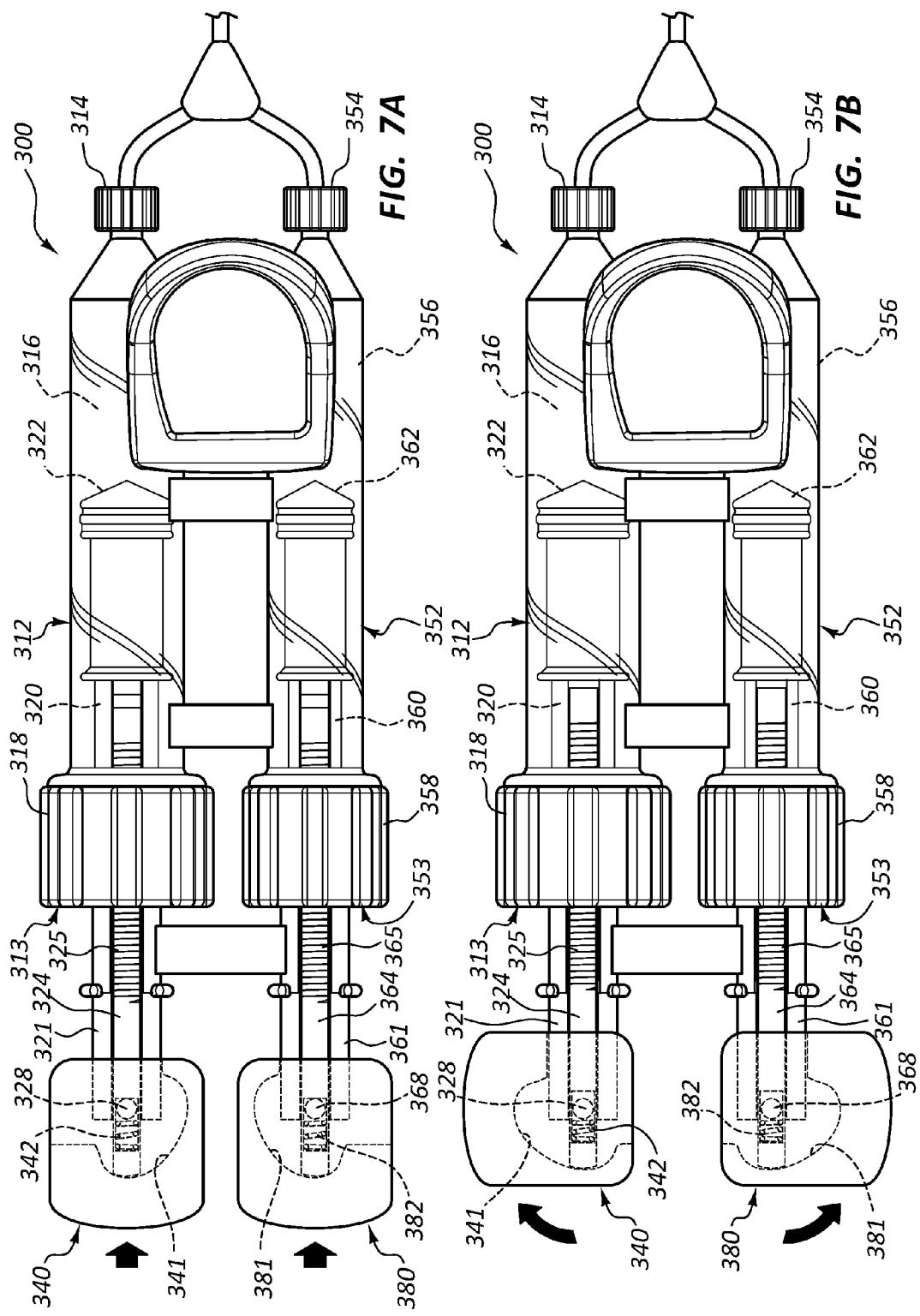

INFLATION DEVICES AND METHODS OF USE THEREOF

RELATED APPLICATIONS

This application claims priority to U.S. Provisional Application No. 61/704,342 filed on Sep. 21, 2012 and titled "Inflation Devices and Methods of Use Thereof," which is hereby incorporated by reference in its entirety.

TECHNICAL FIELD

The present disclosure relates generally to devices and methods used to pressurize, depressurize, or otherwise displace fluid, particularly in medical applications. Certain embodiments relate, more particularly, to devices and methods that selectively couple a plunger to a syringe body by the rotation of a handle. Other embodiments relate, more particularly, to devices and methods that facilitate the generation of high fluid pressure. Such high fluid pressure may be used to inflate a medical device.

BRIEF DESCRIPTION OF THE DRAWINGS

The embodiments disclosed herein will become more fully apparent from the following description and appended claims, taken in conjunction with the drawings. These drawings depict only typical embodiments, which will be described with additional specificity and detail through use of the accompanying drawings in which:

FIG. 3A is a cross-sectional view of the inflation device of FIG. 1A in which the handle is in the first position.

FIG. 3B is a cross-sectional view of the inflation device of FIG. 1A in which the handle is in the second position.

FIG. 6A is a cross-sectional view of the inflation device of FIG. 4 in which the handle is in the first position.

FIG. 6B is a cross-sectional view of the inflation device of FIG. 4 in which the handle is in the second position.

FIG. 7A is a top view of a multiple-plunger inflation device in which each handle is in a first position.

FIG. 7B is a top view of the multiple-plunger inflation device of FIG. 7A in which each handle is in a second position.

DETAILED DESCRIPTION

Figure 1A:
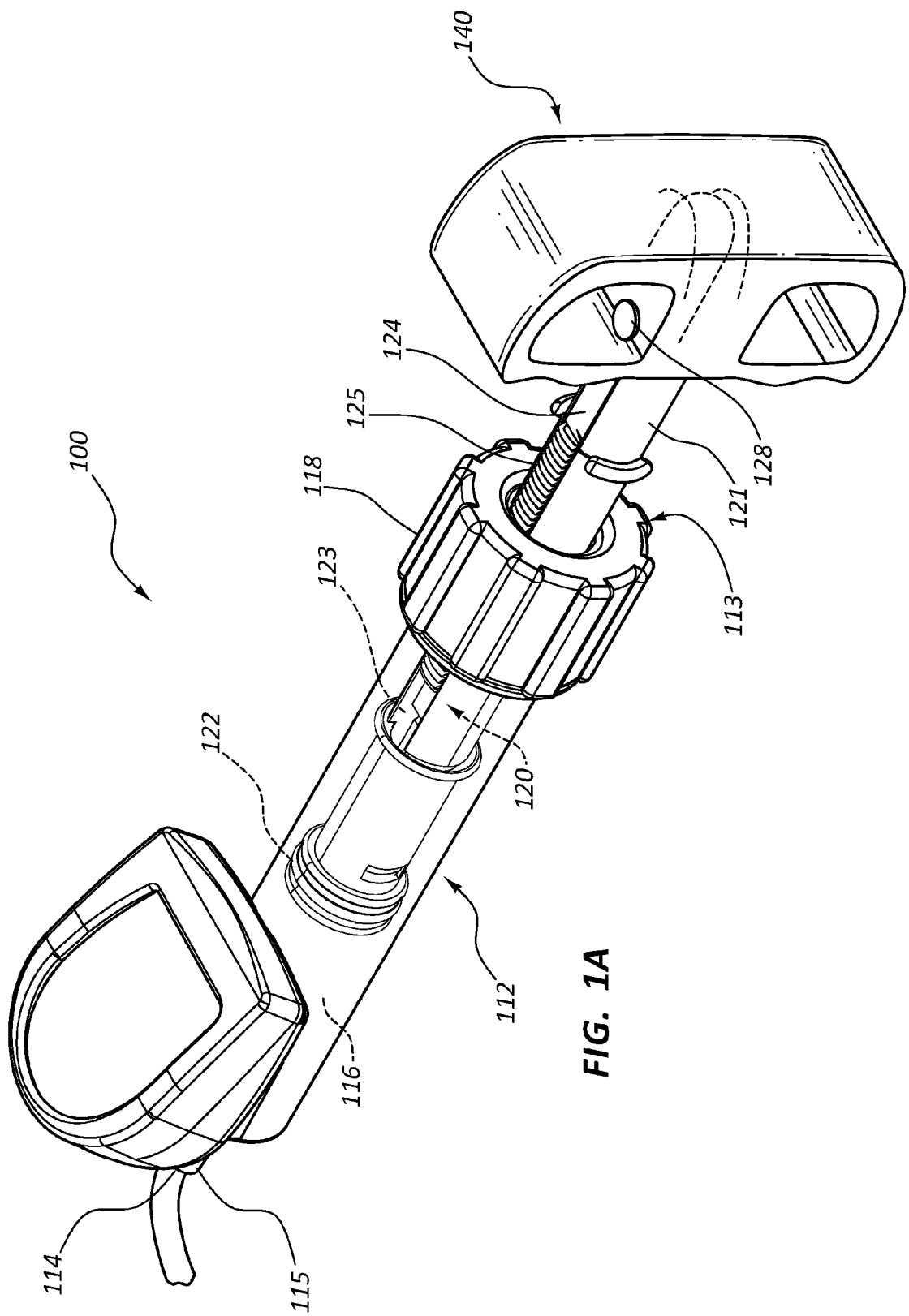
FIG. 1A is a perspective view of an inflation device in which a handle is in a first position.

This disclosure broadly relates to devices and methods that may facilitate the displacement of fluid. Such methods and inflation devices may be used, among other applications, to inflate balloons used in medical procedures (e.g., angioplasty and valvuloplasty).

It will be readily understood by one of ordinary skill in the art having the benefit of this disclosure that the components of the embodiments, as generally described and illustrated in the figures herein, could be arranged and designed in a wide variety of different configurations. Thus, the following detailed description of various embodiments, as represented in the figures, is not intended to limit the scope of the disclosure, but is merely representative of various embodiments. While various aspects of the embodiments are presented in drawings, the drawings are not necessarily drawn to scale unless specifically indicated.

The phrases "connected to," "coupled to," and "in communication with" refer to any form of interaction between two or more entities, including mechanical, electrical, magnetic, electromagnetic, fluidic, and thermal interaction. Two components may be coupled to each other even though they are not in direct contact with each other. For example, two components may be coupled to each other through an intermediate component.

The directional terms "distal" and "proximal" are generally given their ordinary meanings in the art. That is, the distal end of a medical device is the end of the device furthest from the practitioner during ordinary use. The proximal end refers to the opposite end, or the end nearest the practitioner during ordinary use. As specifically applied to a syringe body of an inflation device, the proximal end of the syringe body refers to the end nearest the corresponding handle, and the distal end refers to the opposite end, the end nearest the inlet/outlet port. Thus, if at one or more points in a procedure a practitioner changes the orientation of an inflation device, as used herein, the term "proximal end" always refers to the corresponding handle end (even if the distal end is temporarily closer to the practitioner). The term applies similarly to other components.

"Fluid" is used in its broadest sense, to refer to any fluid, including liquids and gasses as well as solutions, compounds, suspensions, etc., which generally behave as a fluid.

A plunger that is both configured to be disposed within a syringe body and capable of displacing fluid within the syringe body has an "effective surface area" equal to the area of a cross section of the syringe body lumen that is perpendicular to the longitudinal axis of the syringe body.

A "bulbous end" is not restricted to ends having a bulbous shape, but rather comprises any feature at the end of a cable that may restrict the cable end from sliding in at least one direction relative to an inflation device component in contact with the bulbous end.

FIGS. 1A-7B illustrate different views of embodiments of inflation devices. In certain views, the device may be coupled to, or shown with, additional components not included in every view. Further, in some views only selected components are illustrated to provide detail into the relationship of the components. Some components may be shown in multiple views, but not discussed in connection with every view. Disclosure provided in connection with any figure is relevant and applicable to disclosure provided in connection with any other figure.

FIGS. 1A-3B show an embodiment of an inflation device 100. Inflation device 100 comprises three broad groups of primary components: a syringe body 112, a plunger 120, and a handle 140. Each broad group may have numerous subcomponents and parts. The subcomponents and parts that are disclosed herein in connection with these broad groups may be optional. In other words, the terms "syringe body," "plunger," and "handle" are used broadly, referring to the collection of components, but not specifically referring to or requiring the inclusion of any particular component. Use of these terms is non-limiting, as each subcomponent may or may not be present in every embodiment.

The syringe body 112 may be formed of a generally hollow member (e.g., a cylindrical tube) that is configured to receive the plunger 120. The syringe body 112 may include an inlet/outlet port 115 which may be disposed at or adjacent to the distal end 114 of the syringe body 112. In some embodiments, a nut 118 is coupled to the proximal end 113 of the syringe body 112. Such coupling may occur through internal nut threads 119 (FIGS. 3A-3B). The nut 118 may include a center hole configured to allow the plunger 120 to pass through the nut 118 into the syringe body 112. Further, internal nut threads 119 are configured to selectively couple the nut 118 to the plunger 120 in some embodiments (FIGS. 3A-3B).

The plunger 120 may be configured to be longitudinally displaceable within the syringe body 112. The plunger 120 may be comprised of a plunger shaft 121 coupled to a plunger seal 122 at the distal end of the plunger shaft 121. The plunger shaft 121 may also be coupled to the handle 140 at the proximal end of the plunger shaft 121 such that the plunger shaft 121 spans the distance between the plunger seal 122 and the handle 140. The plunger 120 may be configured such that plunger 120 is coupled to the syringe body 112 (for example through threads, ridges, slots, etc.). A component coupled to the syringe body 112 may also be configured to engage with features of the plunger 120 (for example through threads, ridges, slots, etc.). In some embodiments, the plunger 120 includes plunger threads 125 configured to couple the plunger 120 to the nut 118. In such embodiments, rotation of the plunger 120 relative to the syringe body 112 longitudinally displaces the plunger with respect to the syringe body 112 when the threads 125 are coupled to the nut 118 (for example through nut threads 119).

Figure 1B:
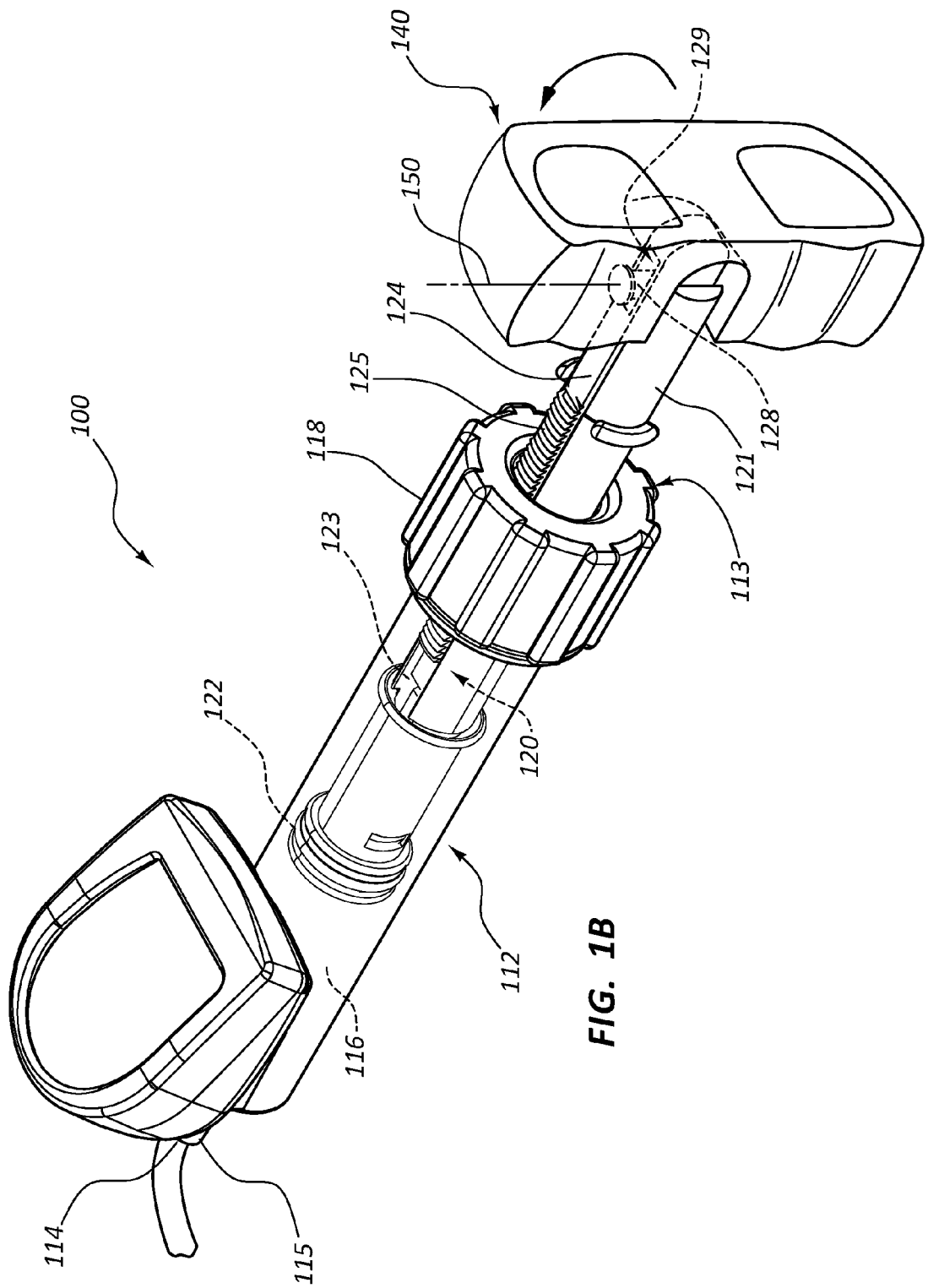
FIG. 1B is a perspective view of the inflation device of FIG. 1A in which the handle is in a second position.

The plunger threads 125 may be configured to either retract within or extend from the plunger shaft 121. Such a configuration may facilitate the coupling and/or uncoupling of a plunger 120 to or from the syringe body 112. As shown in FIGS. 1A and 1B, in some embodiments, the plunger threads 125 do not extend 360 degrees around the axis of the plunger shaft 121. Furthermore, the plunger threads 125 may be formed on a thread rail 124 which is disposed within a groove 123 in the plunger shaft 121. The thread rail 124 may be configured such that angled surfaces 126 on the thread rail 124 and angled surfaces 127 within a groove 123 of the plunger shaft 121 interact such that the plunger threads 125 retract within or extend from the plunger shaft 121. One exemplary relationship between the angled surfaces 126 on the thread rail 124 and the angled surfaces 127 within the groove 123 of the plunger shaft 121 is shown in FIGS. 3A-3B.

Figure 2A:
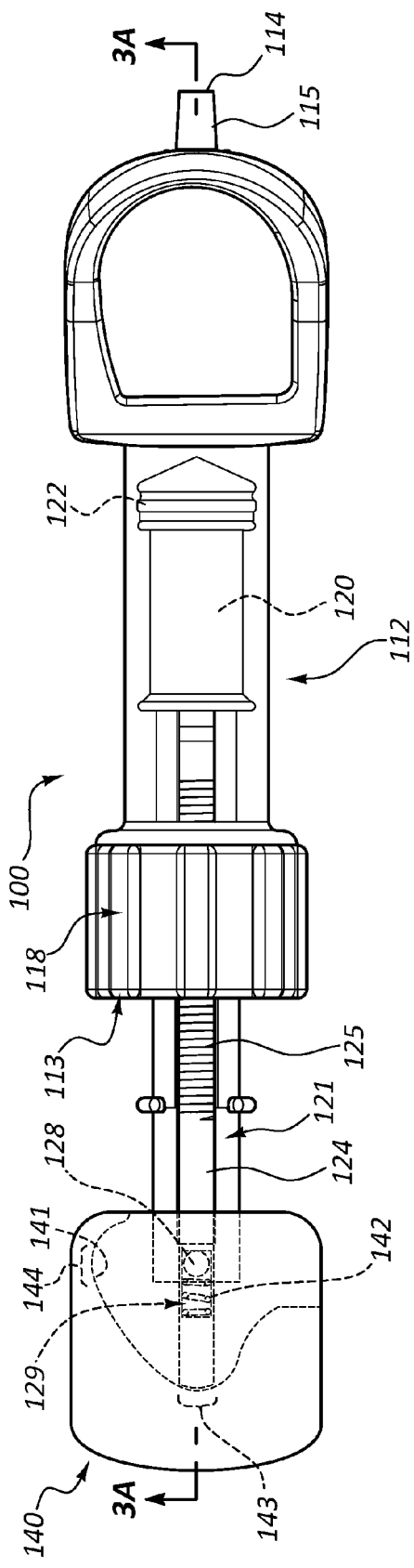
FIG. 2A is a top view of the inflation device of FIG. 1A in which the handle is in the first position.
Figure 2B:
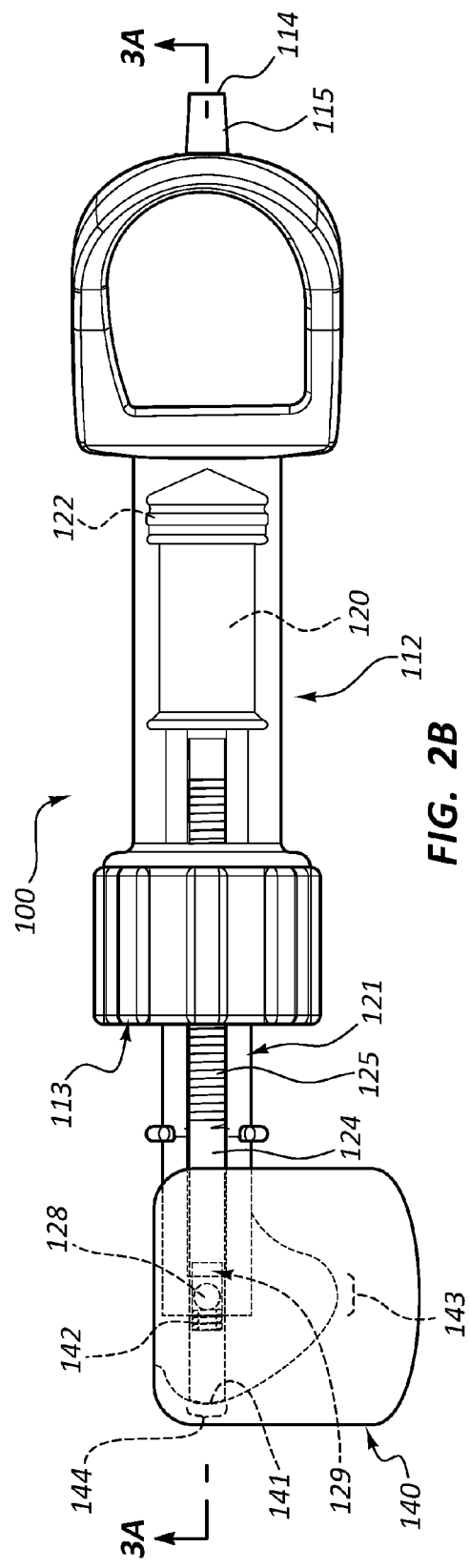
FIG. 2B is a top view of the inflation device of FIG. 1A in which the handle is in the second position.
Figure 4:
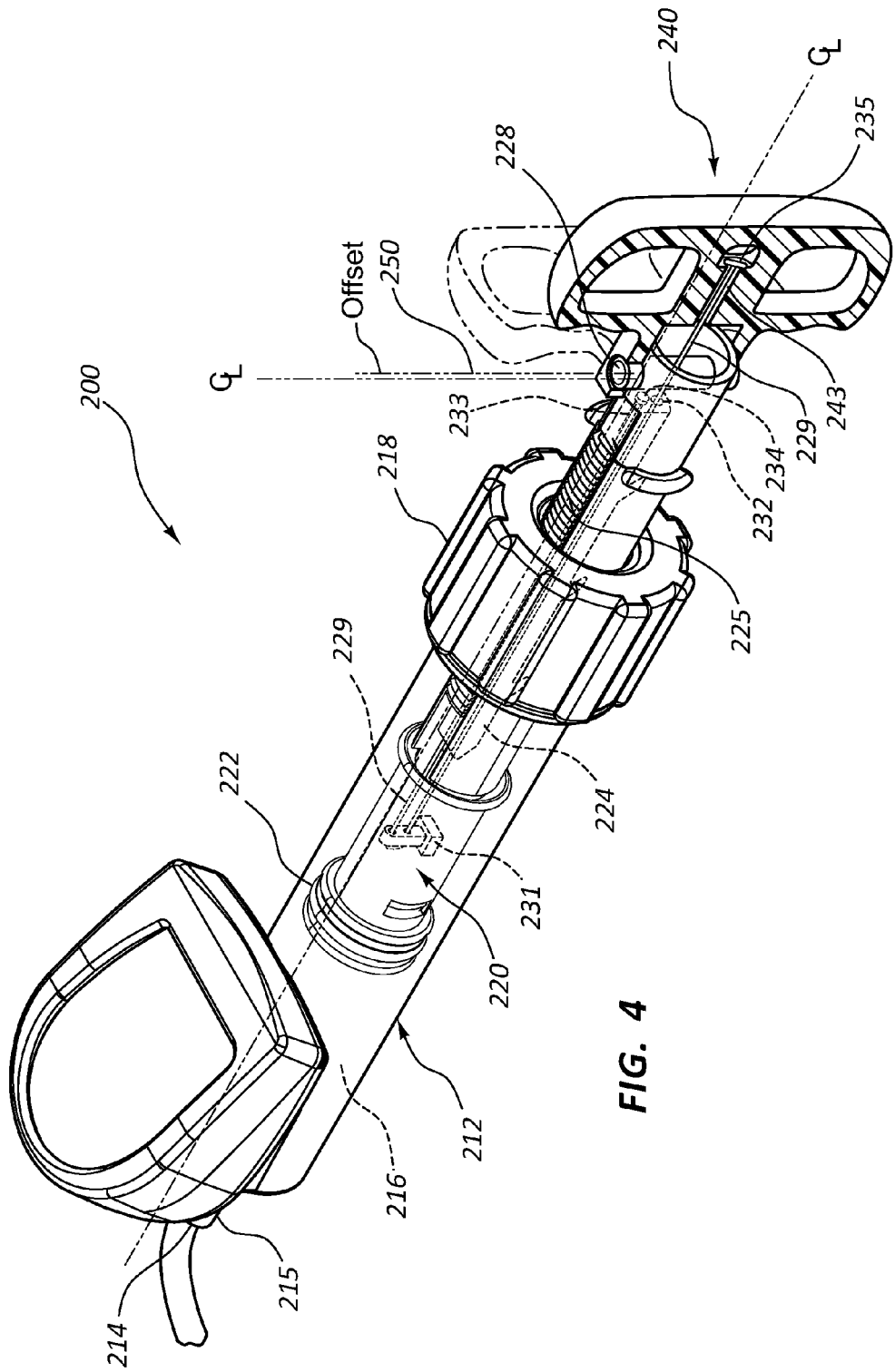
FIG. 4 is a partially cut-away perspective view of another embodiment of an inflation device.
Figure 5A:
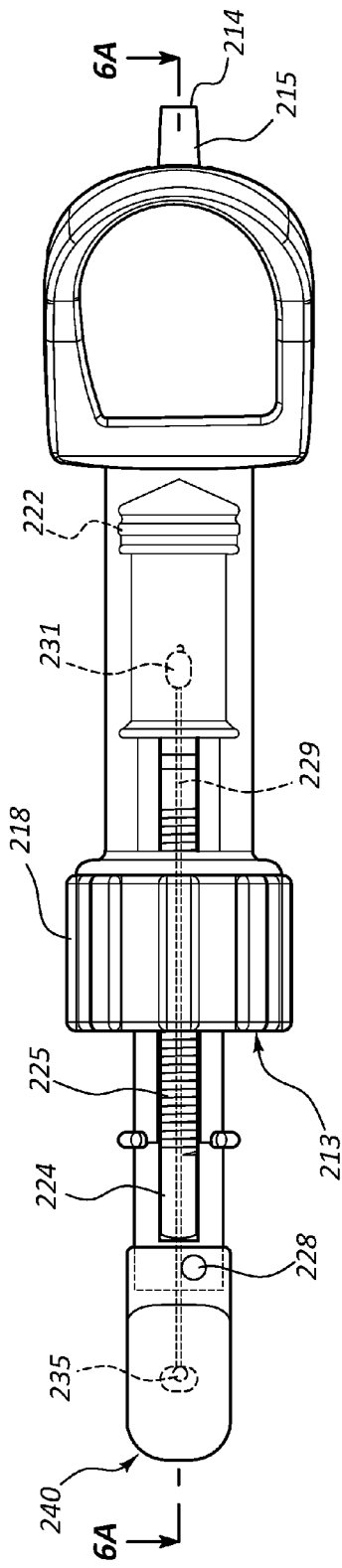
FIG. 5A is a top view of the inflation device of FIG. 4 in which the handle is in a first position.
Figure 5B:
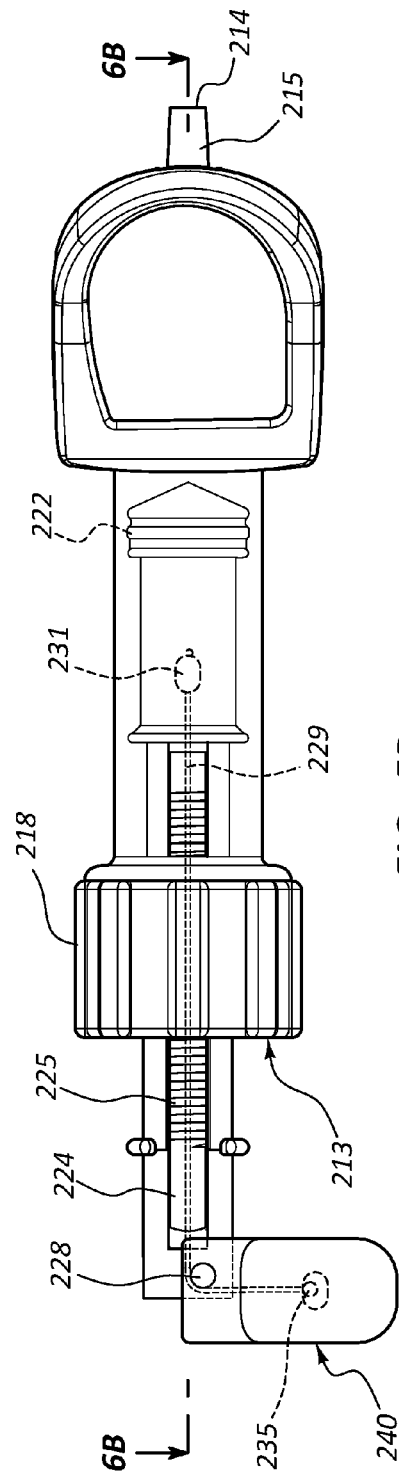
FIG. 5B is a top view of the inflation device of FIG. 4 in which the handle is in a second position.

As illustrated in FIGS. 3A and 3B, translation of the thread rail 124 in the proximal direction simultaneously causes the threads 125 of thread rail 124 to retract toward the center axis of the plunger shaft 121 due to the interaction of the angled surfaces 126 on the threads of thread rail 124 with the angled surfaces 127 in the groove 123 of the plunger shaft 121. Similarly, translation of the thread rail 124 in a distal direction causes the threads 125 of thread rail 124 to move away from the center axis of the plunger shaft 121. Several figures illustrate two possible positions of the thread rail 124 with respect to the internal nut threads 119 and the plunger shaft 121. FIGS. 1B, 2B, and 3B show the thread rail 124 disposed in a non-retracted position, such that the plunger threads 125 engage with the internal nut threads 119. FIGS. 1A, 2A, and 3A show the thread rail 124 sufficiently retracted into the plunger shaft 121 such that the plunger threads 125 do not engage with the internal nut threads 119.

The handle 140 broadly refers to the group of components coupled to the proximal end of the plunger 120, some of which may be configured to be graspable by a user. The handle 140 may comprise an actuator mechanism configured to manipulate inflation device components. In particular, this actuator mechanism may facilitate selective coupling of the plunger 120 to the syringe body 112. For example, manipulation of the handle 140 retracts or extends plunger threads 125 from the plunger shaft 121 such that the plunger threads 125 engage with or disengage from threads coupled to the syringe body 112 (e.g., internal nut threads 119). In some embodiments, the coupling and/or uncoupling of the plunger 120 to or from the syringe body 112 occurs, at least in part, through the rotation of the handle 140 relative to the plunger shaft 121. For example, toggling the handle 140 by rotating it from a first position to a second position will couple or uncouple the plunger 120 to or from the syringe body 112.

FIGS. 2A and 2B show the exemplary embodiment of the inflation device of FIG. 1A from a top view. In the illustrated embodiment, the handle 140 rotates relative to the syringe body 112 about a pin 128. The handle 140 comprises a surface 141 that includes two regions that are not of uniform distance from the axis 150 about which the handle 140 rotates. In some embodiments, the distance from the axis of rotation 150 to a first region 143 of surface 141 that contacts the thread rail 124 when the handle 140 is in the first position (FIG. 2A) is greater than the distance from the axis of rotation 150 to a second region 144 in contact with the thread rail 124 when the handle 140 is in the second position (FIG. 2B). The surface 141 may contain nubs or catches that may prevent the thread rail 124 from inadvertently sliding along the surface 141 when the handle 140 is in a position desired by the practitioner.

In some embodiments, the surface 141 will comprise an intervening region between the first region 143 and the second region 144 that contacts the thread rail 124 as the handle transitions from the first position to the second position (or vice versa). The distance from the axis of rotation to any point along this intervening region may be less than the greater of the distance from the axis of rotation 150 to the first region 143 or the second region 144 and greater than the lesser of the distance from the axis of rotation 150 to the first region 143 or the second region 144.

In one embodiment, a spring 142 biases the thread rail 124 to interact with surface 141. As illustrated in FIGS. 2A and 2B, the spring 142 is situated within a slot 129 of the thread rail 124, extending from the pin 128 to a proximal interior surface of the slot 129. When the handle 140 is in the first position such that the thread rail 124 interacts with the first region 143 of surface 141 (shown in FIG. 2A), the plunger threads 125 are retracted within the plunger shaft 121 and are not coupled to the syringe body 112.

By rotating the handle 140 from the first position to the second position, thread rail 124 (which is biased to interact with the surface 141 due to the spring 142) follows along the surface 141. Because the distance from the region of the surface 141 in contact with the thread rail 124 to the axis of rotation 150 decreases as the handle 140 is transitioned from the first position to the second position, rotation of the handle 140 from the first position to the second position compresses the spring 142 between the surface of the slot 129 and the pin 128, causing the thread rail 124 to be longitudinally displaced in a distal direction. In the embodiment shown in FIGS. 2A and 2B, displacement of the thread rail 124 in the distal direction extends plunger threads 125 from the plunger shaft 121 and couples the plunger 120 to the syringe body 112. However, it will be appreciated by one of ordinary skill in the art having the benefit of this disclosure that it is also within the scope of this disclosure to modify the angles of the angled surfaces 126 on the thread rail 124 and the angles of the angled surfaces 127 within the groove 123 such that a displacement of the thread rail 124 in the distal direction would retract the plunger threads 125.

Likewise, it is within the scope of this disclosure to alter the orientation of surface 141 within handle 140 from that shown in FIGS. 2A-2B. For example, the inflation device may be configured such that when the thread rail is in contact with a region of the surface that is closer than another region of the surface to the axis of rotation, the handle is positioned so that a plane that substantially bisects the thread rail (e.g., the plane that defines the cross section shown in FIGS. 3A-3B) substantially bisects that handle as well.

A fluid reservoir 116 may be defined by the space enclosed by the inside walls of the syringe body 112 between the plunger seal 122 and the distal end 114 of the syringe body 112. Accordingly, movement of the plunger 120 with respect to the syringe body 112 will alter the volume of the fluid reservoir 116. Such movement may occur by one or more methods. In one method, the plunger threads 125 are retracted and opposing forces are applied on the plunger shaft 121 and the syringe body 112. (These forces may displace the plunger shaft 121 distally or proximally with respect to the syringe body 112.) This method may be useful when a practitioner desires to quickly displace the plunger shaft 121, for instance, while priming the inflation device or while priming or deflating an attached medical device such as a balloon. A practitioner may also use this method to quickly fill the reservoir 116 with fluid by disengaging the plunger threads 125 and pulling the plunger shaft 121 in a proximal direction with respect to the syringe body 112. Furthermore, a practitioner may quickly force fluid into lines leading to another device or quickly expel unwanted air bubbles from the reservoir 116 by retracting the plunger threads 125 and repositioning the plunger shaft 121.

In another method, when the threads 125 engage with internal nut threads 119, the plunger 120 may be displaced relative to the syringe body 112 by rotating the plunger shaft 121 relative to the syringe body 112 (and the subsequent interaction of threads). In certain embodiments, the plunger shaft 121 may be rotated by rotating a handle 140 that is coupled to the plunger shaft 121. Such rotation of the handle 140 may be about a longitudinal axis of the plunger. This method may give a practitioner more precise control over the position of the plunger shaft 121 (for example when displacing the plunger shaft 121 in order to adjust the fluid pressure within the reservoir 116). Further, the threads may provide a mechanical advantage to displace the plunger shaft 121 in instances where high fluid pressure within the reservoir 116 makes displacement difficult or impossible. In these instances, the practitioner may opt to displace the plunger shaft 121 by rotation of the plunger shaft 121. Both methods of displacement (i.e., by applying opposing forces on a syringe body and plunger and by rotation of a plunger shaft relative to a syringe body) may be utilized during the course of a single therapy.

A practitioner may use the following procedure in connection with inflation device 100 to inflate a medical device. Similar procedures may be used with other inflation device embodiments later disclosed in this application. First, the practitioner introduces fluid into fluid reservoir 116 by connecting the distal tip 115 of the syringe body 112 with a desired fluid and retracting the plunger 120 within syringe body 112. Second, the practitioner connects a medical device to the distal tip 115 of the syringe body 112. Third, the practitioner displaces fluid within the fluid reservoir 116 by advancing the plunger 120 within the syringe body 112. Fourth, when the practitioner is unable (or otherwise finds it disadvantageous) to further advance the plunger 120 within the syringe body 112 (for example due to an increase of fluid pressure within the fluid reservoir 116), the practitioner locks the plunger in place relative to the syringe body by rotating the handle relative to the plunger shaft 121. By this step, a practitioner, without further exertion, may prevent the displacement of the plunger 120 with respect to the syringe body 112 (such as proximal displacement due to fluid pressure within the fluid reservoir 116). Fifth, the practitioner rotates handle 140 relative to the syringe body 112 about the longitudinal axis of the plunger 120. Again, due to the interaction of threads 125 with internal nut threads 119, such rotation may be utilized to advance or retract the plunger within the syringe body 112.

FIGS. 4A-6B illustrate an embodiment of an inflation device 200 where a plunger 220 is coupled to and/or uncoupled from a syringe body 212 through the displacement of a cable 229. Such displacement may occur through rotation of a handle 240 relative to a plunger shaft 221. The cable 229 may be coupled to plunger threads 225 that are selectively coupleable to the syringe body 212. For example, a first bulbous end 235 of the cable 229 may secure a first end of the cable within the handle 240. The handle 240 may include a channel 243 configured such that a region of the cable 229 may be slidably disposed within the channel 243. A second end of the cable 229 may be coupled to the thread rail 224 (e.g., through the direct interaction of the thread rail 224 with a second bulbous end 234). A region of the cable 229 situated between the first end and the second end may interact with an inflation device component (or inflation device components) such that the cable 229 extends along a curved path. This cable 229 may comprise extended regions that are substantially parallel to each other. The cable 229 extending along a curved path may enable a practitioner, by applying force on the first end of the cable 229, to exert a force on the second end of the cable 229 in a direction different from that applied to the first end. As shown in the illustrated embodiment of FIGS. 4-6B, the cable 229 is coupled to a support structure 231 in a manner that bends the cable 229 along a curved path such that the cable runs in two opposing directions. While, in the illustrated embodiment, the bend is accomplished by threading the cable 229 through the support structure 231, the cable 229 need not be threaded through support structure channels. For example, the cable 229 may simply bend around an inflation device component.

As further illustrated in FIGS. 4-6B, the cable 229 may extend through a region or regions of a plunger shaft 221. For example, the cable 229 can extend through a channel or channels through which the cable 229 is slidably disposed. In an exemplary embodiment (shown in FIG. 4), the cable 229 extends through both a first channel 232 and a second channel 233 within the thread rail 224.

Rotation of the handle 240 from a first position to a second position may displace the cable 229, causing the second bulbous end 234 to longitudinally displace the thread rail 224 toward the distal end of the plunger 220. As illustrated in FIGS. 4-6B, such displacement arises from the rotation of the handle 240 relative to the plunger shaft 221 such that cable 229 is pulled about the surface of a pin 228. In this embodiment, due to the non-negligible radius of the pin 228 (which makes the surface of the pin 228 not coincident with the axis of rotation 250), cable 229 is pulled across the surface of the pin 228 as the handle 240 is toggled from the first position to the second position. It will be appreciated by one of ordinary skill in the art having the benefit of this disclosure that it is within the scope of this disclosure to alter the size and/or shape of the surface of the pin 228 to increase or decrease the distance over which thread rail 224 is longitudinally displaced. Likewise, it also within the scope of the disclosure to configure a device such that rotation of a handle relative to the plunger shaft displaces a cable that passes over a surface other than a pin.

A practitioner may use inflation device 200 to inflate a medical device through procedures similar to those described in connection with inflation device 100, as discussed above. For example, a practitioner may introduce fluid into the fluid reservoir 216, attach the inflation device 200 to a medical device, advance the plunger 220 to displace fluid, rotate the handle 240 relative to the plunger shaft 221 to lock the plunger 220 with respect to the syringe body 212, and displace the plunger 220 through subsequent rotation of the handle 240 about the longitudinal axis of the plunger 220.

In inflation device 200, as compared to inflation device 100, as discussed above, rotation of the handle 240 relative to the plunger shaft 221 results in engagement of threads 225 with internal nut threads 219 (thereby locking plunger 220 in place relative to the syringe body 212) through a different mechanism. By rotating the handle 240 relative to the plunger shaft 221, the cable 229 is pulled about the pin 228. By pulling cable 229 about the pin 228, the second bulbous end 234 displaces thread rail 224 such that threads 225 engage with internal nut threads 219. Such engagement of threads 225 with internal nut threads 219 locks the plunger 220 in place.

Multiple-plunger inflation devices, such as those shown in FIGS. 7A-7B, may facilitate the generation of relatively high fluid pressures to inflate medical devices. In many instances, the amount of force needed to displace fluid within a fluid reservoir varies as a plunger is advanced or retracted within a syringe body. For example, the amount of force needed to advance a plunger within a syringe body may increase as pressure within the corresponding fluid reservoir increases. In particular, the need for variable force inputs in order to advance a plunger and inflate a medical device may arise in angioplasty or valvuloplasty procedures. Furthermore, the force needed to displace a given volume of fluid may be a function of the effective surface area of a plunger. Thus, because the force needed to advance a plunger within a syringe body to displace fluid may not be uniform, it may be beneficial for a practitioner to use an inflation device having more than one plunger, each having a different effective surface area.

FIGS. 7A and 7B provide top views of a multiple-plunger inflation device 300. In the illustrated embodiment, inflation device 300 comprises a first syringe body 312 and a second syringe body 352 with a first plunger 320 and a second plunger 360. The first syringe body 312 and the first plunger 320 have larger diameters than the second syringe body 352 and the second plunger 360. The fluid reservoirs 316 and 356, associated with syringe bodies 312 and 352 respectively, are connected such that both are in fluid communication with each other and any connected medical device.

To facilitate the displacement of fluid using device 300, the practitioner may advance (i.e., displace toward the distal end 314 of the syringe body 312) and lock in place a first plunger 320 (having a particular effective surface area) then subsequently advance (i.e., displace toward the distal end 354 of the syringe body 352) a second plunger 360 having a smaller effective surface area than the first plunger 320. The first plunger may be locked in place by rotating the first handle 340 such that the first thread rail 324 engages with the internal nut threads of nut 318. In this manner, the practitioner may displace fluid by advancing the plunger 320 a shorter distance within a syringe body than that which would have been needed to displace an equal volume of fluid using only the second plunger 360 in the second syringe body 352. Furthermore, the decreased effective surface area of the second plunger 360 may allow the practitioner to continue increasing the fluid pressure without needing to apply a force with as large a magnitude as that which would have been needed to displace fluid using the first plunger 320 alone. This process may also permit the practitioner to displace fluid more quickly than by attempting to advance either plunger alone.

Without further elaboration, it is believed that one skilled in the art can use the preceding description to utilize the present disclosure to its fullest extent. The examples and embodiments disclosed herein are to be construed as merely illustrative and exemplary, and not as limitations of the scope of the present disclosure in any way. It will be apparent to those having skill in the art that changes may be made to details of the above-described embodiments without departing from the underlying principles of the disclosure herein. It is intended that the scope of the invention be defined by the claims appended hereto and their equivalents.

The invention claimed is:

1. An inflation device configured to displace fluid, the inflation device comprising:
   a syringe body;
   a plunger configured to be disposed within the syringe body, the plunger selectively coupleable to the syringe body, wherein the plunger comprises a plunger shaft; and
   a handle rotatably coupled to the plunger shaft,
   wherein rotation of the handle in a transverse direction relative to a longitudinal axis of the plunger shaft selectively couples and decouples the plunger to and from the syringe body.

2. The inflation device of claim 1, wherein the handle is rotatably coupled to the plunger shaft about a pin.

3. The inflation device of claim 1, wherein the plunger, when coupled to the syringe body, is coupled to the syringe body by a plurality of threads.

4. The inflation device of claim 1, wherein the plunger, when coupled to the syringe body, is coupled to the syringe body by the engagement of a plurality of threads with a thread rail, wherein engagement of the plurality of threads with the thread rail restricts the movement of the plunger within the syringe body.

5. The inflation device of claim 4, wherein the handle comprises a surface configured to interact with the thread rail, wherein rotation of the handle relative to the plunger shaft displaces the thread rail in a longitudinal direction due to interaction of the thread rail with the surface.

6. The inflation device of claim 5, wherein the thread rail comprises a slot configured to accept a spring, wherein the spring biases the thread rail to interact with the surface.

7. The inflation device of claim 1, further comprising a cable that is coupled to a thread rail, wherein, by rotating the handle relative to the plunger shaft, the cable is displaced, and the thread rail is displaced in a longitudinal direction.

8. A method of coupling or decoupling a plunger component to or from a syringe body in an inflation device comprising:
   obtaining an inflation device comprising: a syringe body; a plunger comprising a plunger shaft disposed within the syringe body and a handle rotatably coupled to the plunger shaft; and
   rotating the handle in a transverse direction relative to a longitudinal axis of the plunger shaft to selectively couple or decouple the plunger to or from the syringe body.

9. The method of claim 8, wherein the handle is rotated about a pin.

10. The method of claim 8, further comprising engaging or disengaging a plurality of threads with a thread rail in response to rotating the handle, wherein engaging the plurality of threads with the thread rail restricts the movement of the plunger within the syringe body, and disengaging the plurality of threads with the thread rail permits movement of the plunger within the syringe body.

11. An inflation device configured to displace fluid, the inflation device comprising:
  a syringe body;
  a plunger configured to be disposed within the syringe body, the plunger selectively coupleable to the syringe body, wherein the plunger comprises a plunger shaft; and
  a handle rotatably coupled to the plunger shaft such that the handle rotates about an axis of rotation,
  wherein rotation of the handle relative to the plunger shaft selectively couples and decouples the plunger to and from the syringe body; and
  wherein the axis of rotation of the handle is disposed at an angle with respect to a longitudinal axis of the plunger shaft.

12. The inflation device of claim 11, wherein the handle is rotatably coupled to the plunger shaft about a pin.

13. The inflation device of claim 11, wherein the plunger, when coupled to the syringe body, is coupled to the syringe body by a plurality of threads.

14. The inflation device of claim 11, wherein the plunger, when coupled to the syringe body, is coupled to the syringe body by the engagement of a plurality of threads with a thread rail, wherein engagement of the plurality of threads with the thread rail restricts the movement of the plunger within the syringe body.

15. The inflation device of claim 14, wherein the handle comprises a surface configured to interact with the thread rail, wherein rotation of the handle relative to the plunger shaft displaces the thread rail in a longitudinal direction due to interaction of the thread rail with the surface.

16. The inflation device of claim 15, wherein the thread rail comprises a slot configured to accept a spring, wherein the spring biases the thread rail to interact with the surface.

17. The inflation device of claim 11, further comprising a cable that is coupled to a thread rail, wherein, by rotating the handle relative to the plunger shaft, the cable is displaced, and the thread rail is displaced in a longitudinal direction.

18. The inflation device of claim 11, wherein the axis of rotation of the handle is disposed at an orthogonal angle with respect to the longitudinal axis of the plunger shaft.

19. A method of coupling or decoupling a plunger component to or from a syringe body in an inflation device comprising:
  obtaining an inflation device comprising: a syringe body; a plunger comprising a plunger shaft disposed within the syringe body and a handle rotatably coupled to the plunger shaft; and
  rotating the handle about an axis of rotation to selectively couple or decouple the plunger to or from the syringe body;
  wherein the axis of rotation is disposed at an angle with respect to a longitudinal axis of the plunger shaft.

20. The method of claim 19, wherein the handle is rotated about a pin.

21. The method of claim 19, further comprising engaging or disengaging a plurality of threads with a thread rail in response to rotating the handle, wherein engaging the plurality of threads with the thread rail restricts the movement of the plunger within the syringe body, and disengaging the plurality of threads with the thread rail permits movement of the plunger within the syringe body.

22. The method of claim 19, wherein the axis of rotation of the handle is disposed at an orthogonal angle with respect to the longitudinal axis of the plunger shaft.

* * * * *